(12) United States Patent
Blaney et al.

(10) Patent No.: US 6,177,607 B1
(45) Date of Patent: Jan. 23, 2001

(54) ABSORBENT PRODUCT WITH NONWOVEN DAMPNESS INHIBITOR

(75) Inventors: Carol Ann Blaney, Roswell; Ann Louis McCormack, Cumming; Susan Carol Paul, Alpharetta, all of GA (US)

(73) Assignee: Kimberly-Clark Worldwide, Inc., Neenah, WI (US)

( * ) Notice: Under 35 U.S.C. 154(b), the term of this patent shall be extended for 0 days.

(21) Appl. No.: 09/344,025

(22) Filed: Jun. 25, 1999

(51) Int. Cl.⁷ ...................................... A61F 13/15
(52) U.S. Cl. .................. 604/378; 442/370; 442/394; 442/398; 604/384; 604/385.1
(58) Field of Search .................. 442/370, 394, 442/398; 525/240; 428/315.5; 604/378, 384, 385.1

(56) References Cited

U.S. PATENT DOCUMENTS

| | | | |
|---|---|---|---|
| 3,338,992 | 8/1967 | Kinney | 264/24 |
| 3,341,394 | 9/1967 | Kinney | 161/72 |
| 3,502,538 | 3/1970 | Petersen | 161/150 |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,901,236 | 8/1975 | Assarsson et al. | 128/284 |
| 4,041,203 | 8/1977 | Brock et al. | 428/157 |
| 4,076,663 | 2/1978 | Masuda et al. | 260/17.4 GC |
| 4,286,082 | 8/1981 | Tsubakimoto et al. | 526/240 |
| 4,306,559 | 12/1981 | Nishizawa et al. | 128/287 |
| 4,340,563 | 7/1982 | Appel et al. | 264/518 |
| 4,681,793 | 7/1987 | Linman et al. | 428/138 |
| 4,758,239 * | 7/1988 | Yeo et al. | 604/366 |
| 4,818,600 | 4/1989 | Braun et al. | 428/290 |
| 5,043,203 | 8/1991 | Boissé et al. | 428/233 |
| 5,272,236 | 12/1993 | Lai et al. | 526/348.5 |
| 5,294,478 | 3/1994 | Wanek et al. | 428/218 |
| 5,300,054 | 4/1994 | Feist et al. | 604/378 |
| 5,304,161 | 4/1994 | Noel et al. | 604/378 |
| 5,322,728 | 6/1994 | Davey et al. | 428/296 |
| 5,344,698 | 9/1994 | Rock et al. | 428/253 |
| 5,346,487 | 9/1994 | Lovestedt | 604/385.1 |
| 5,387,209 | 2/1995 | Yamamoto et al. | 604/384 |
| 5,401,267 | 3/1995 | Couture-Dorschner et al. | 604/384 |
| 5,437,653 | 8/1995 | Gilman et al. | 604/378 |

(List continued on next page.)

FOREIGN PATENT DOCUMENTS

| | | | |
|---|---|---|---|
| 0 813 848 A1 | 12/1997 | (EP) | A64F/13/15 |
| 0 893 113 A1 | 1/1999 | (EP) | A61F/13/15 |
| 0 953 324 | 11/1999 | (EP) | A61F/13/15 |
| 96/19346 | 6/1996 | (WO) | B32B/7/00 |
| 96/21409 | 7/1996 | (WO) | A61F/13/00 |
| 97/16148 | 5/1997 | (WO) | A61F/13/15 |
| 97/24095 | 7/1997 | (WO) | A61F/13/15 |
| 97/24097 | 7/1997 | (WO) | A61F/13/15 |
| 97/34557 | 9/1997 | (WO) | A61F/13/15 |
| 97/36562 | 10/1997 | (WO) | A61F/13/15 |
| 98/27920 | 7/1998 | (WO) | A61F/13/15 |
| 98/29480 | 7/1998 | (WO) | C08J/5/18 |

\* cited by examiner

Primary Examiner—John G. Weiss
Assistant Examiner—Michele Kidwell
(74) Attorney, Agent, or Firm—Pauley Peterson Kinne & Fejer

(57) ABSTRACT

An absorbent article including a liquid-permeable top layer, an absorbent core layer, a breathable outer cover, and an inner nonwoven filament layer between the absorbent core and breathable outer cover. The outer cover includes a breathable film and an outer nonwoven filament layer. The inner nonwoven filament layer has a mean fiber denier which is higher than the mean fiber denier of the outer nonwoven filament layer. The inner nonwoven filament layer serves as a dampness inhibitor which reduces or prevents perceived dampness on the external surface of the outer cover by lowering thermal conductivity between the absorbent core and the outer cover surface.

32 Claims, 2 Drawing Sheets

U.S. PATENT DOCUMENTS

| | | | |
|---|---|---|---|
| 5,439,458 | 8/1995 | Noel et al. | 604/378 |
| 5,460,622 | 10/1995 | Dragoo et al. | 604/378 |
| 5,466,513 | 11/1995 | Wanek et al. | 428/218 |
| 5,527,303 | 6/1996 | Milby, Jr. et al. | 604/385.1 |
| 5,558,658 | 9/1996 | Menard et al. | 604/385.1 |
| 5,569,233 | 10/1996 | Goulait | 604/391 |
| 5,571,096 | 11/1996 | Dobrin et al. | 604/383 |
| 5,571,619 | 11/1996 | McAlpin et al. | 428/364 |
| 5,591,297 | 1/1997 | Ahr | 156/521 |
| 5,603,707 | 2/1997 | Trombetta et al. | 604/383 |
| 5,626,571 * | 5/1997 | Young et al. | 604/370 |
| 5,643,239 | 7/1997 | Bodford et al. | 604/370 |
| 5,680,653 * | 10/1997 | Mathis et al. | 2/123 |
| 5,810,797 | 9/1998 | Menard et al. | 604/378 |
| 5,817,081 | 10/1998 | LaVon et al. | 604/378 |
| 5,843,066 | 12/1998 | Dobrin | 604/385.1 |
| 5,914,184 * | 6/1999 | Morman | 428/315.9 |
| 5,928,209 | 7/1999 | Bodford et al. | 604/370 |
| 5,932,316 | 8/1999 | Cree et al. | 428/182 |
| 5,955,187 * | 9/1999 | McCormack et al. | 428/315.5 |
| 6,015,764 * | 1/2000 | McCormack et al. | 442/370 |
| 6,037,281 * | 3/2000 | Mathis et al. | 442/394 |
| 6,072,005 * | 6/2000 | Kobylivker et al. | 525/240 |

ABSORBENT PRODUCT WITH NONWOVEN DAMPNESS INHIBITOR

FIELD OF THE INVENTION

The present invention is directed to an absorbent product having at least a top layer, an absorbent core, and a breathable outer cover material. A fibrous nonwoven web having fibers of relatively high denier is disposed between the absorbent core and the breathable outer cover, causing a reduction in surface dampness on the outer surface of the breathable outer cover material when the absorbent core is wet without significantly reducing breathability of the outer cover when the absorbent product is dry.

BACKGROUND OF THE INVENTION

Absorbent articles, such as diapers, child training pants, adult incontinence garments, swim wear and the like, typically include at least a liquid-permeable top layer for direct contact with the wearer, an absorbent core layer, and a substantially liquid-impermeable outer cover material. The absorbent core is positioned between the top layer and the outer cover material. When the absorbent article is exposed to a liquid insult, liquid passes through the top layer and into the absorbent core. The outer cover prevents the liquid in the absorbent core from leaving the garment.

Many of today's absorbent garments utilize breathable outer cover materials. Breathable outer cover materials are substantially impermeable to liquids, but are permeable to water vapor. Breathable outer cover materials permit escape of water vapor from the absorbent garment, increasing the garment comfort and reducing skin rashes and other irritations that result when water vapor is trapped inside the garment and heated by the wearer's body. Many of today's absorbent garments are highly breathable, for maximum wearer comfort.

One shortcoming of breathable absorbent articles is a cold, damp, clammy feel that often occurs on the outside of the garment, i.e., on the outside of the outer cover material. As liquid water in the absorbent core evaporates and passes through the outer cover material, the associated evaporative cooling causes a lowering of temperature of the absorbent core and adjacent outer cover material, resulting in a clammy, damp-feeling outer cover. There is thus a need or desire in the absorbent garment industry for absorbent articles which are highly breathable, yet which reduce or avoid the perceived dampness caused by evaporative cooling.

SUMMARY OF THE INVENTION

The present invention is directed to an absorbent article having a breathable outer cover material and reduced perceived outer cover dampness. The absorbent article includes at least a liquid-permeable top layer, a breathable, substantially liquid impermeable outer cover material, and an absorbent core layer between the top layer and the outer cover material. The outer cover material includes a breathable film laminated to a nonwoven filament web, and is positioned with the film facing inward (i.e., toward the absorbent core) and with the nonwoven web facing outward. In accordance with the invention, a second nonwoven filament web is interposed between the absorbent core and the breathable outer cover material. The filaments of the second nonwoven web have a mean denier which is higher than the mean denier of the filaments of the first nonwoven web in the outer cover material.

The presence of the second (inner) nonwoven filament web, having the higher denier filaments, reduces dampness of the exposed surface of the first nonwoven web, by providing an air gap between the absorbent core and outer cover. This air gap separates the absorbent core from the outer cover, and provides thermal insulation between the cooled absorbent core and the fingers of the hand touching the outer cover. The thermal conductivity of the outer cover system is thus lowered, and heat from the hand is lost to a lesser degree. This results in a perceived warmer and drier diaper surface. The clammy and cold feelings are reduced, promoting perceptions of dryness and clothlike feel.

At deniers of 2 and higher, the inner nonwoven web generally possesses high enough bulk to provide sufficient thermal insulation. At deniers less than 2, the nonwoven web of the outer cover possesses an excellent clothlike feel.

With the foregoing in mind, it is a feature and advantage of the invention to provide an absorbent article with a breathable outer cover system whose thermal conductivity is favorably decreased by the addition of a nonwoven web with fibers greater than 2 denier between the outer cover and absorbent core.

It is also a feature and advantage of the invention to provide a breathable absorbent article having a dampness-inhibiting layer which does not inhibit breathability.

It is also a feature and advantage of the invention to provide an absorbent article having a breathable outer cover which remains warm and dry to the touch under a wide variety of conditions.

The foregoing and other features and advantages will become further apparent from the following detailed description of the presently preferred embodiments, read in conjunction with the accompanying examples and drawings. The detailed description, examples and drawing are intended to be illustrative rather than limiting, the scope of the invention being defined by the appended claims and equivalents thereof.

DEFINITIONS

Figure 1:
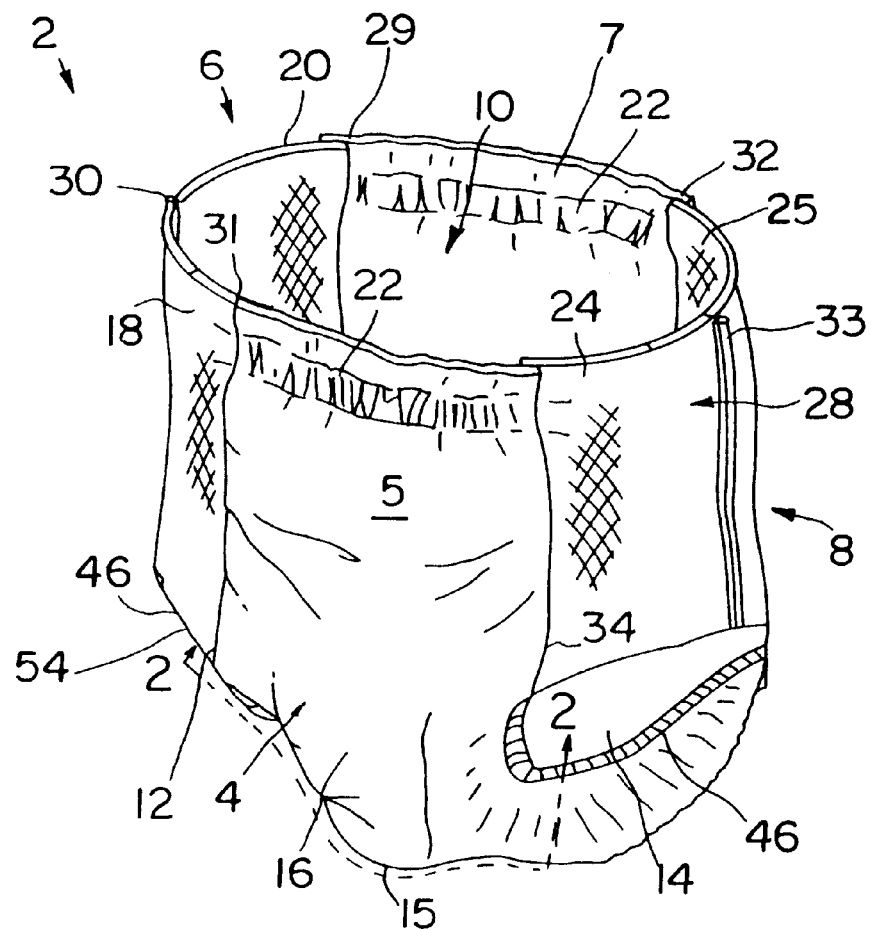
FIG. 1 is a perspective view of an absorbent article of the invention.

The terms "breathable film," "breathable laminate" or "breathable outer cover material" refer to a film, laminate, or outer cover material having a water vapor transmission rate ("WVTR") of at least about 300 grams/$m^2$-24 hours, using the WVTR Test Procedure described herein.

The term "outer cover system" refers to an outer cover laminate in combination with a second, inner dampness-inhibiting nonwoven web.

The term "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, and bonded carded web processes. Pulp or cellulose-based webs are also nonwoven. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

The term "microfibers" means small diameter fibers typically having an average fiber denier of about 0.005–10, for example, having an average fiber denier of about 0.05–6, or more particularly, microfibers may have an average fiber denier of about 1–4.

The term "denier" is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex," which is defined as the grams per kilometer of fiber. Tex may be calculated as denier/9. The "mean fiber denier" is the sum of the deniers for each fiber, divided by the number of fibers.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3 microns, more particularly, between about 0.6 and 10.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

The term "film" refers to a thermoplastic film made using a film extrusion process, such as a cast film or blown film extrusion process. The term "water-permeable porous films" refers to films rendered porous by puncturing or aperturing, and to films rendered porous by mixing polymer with filler, forming a film from the mixture, and stretching the film.

The term "polymer" includes, but is not limited to, homopolymers, copolymers, such as for example, block, graft, random and alternating copolymers, terpolymers, etc. and blends and modifications thereof. Furthermore, unless otherwise specfically limited, the term "polymer" shall include all possible geometrical configurations of the material. These configurations include, but are not limited to isotactic, syndiotactic and atactic symmetries.

The term "pulp fibers" refers to fibers from natural sources such as woody and non-woody plants. Woody plants include, for example, deciduous and coniferous trees. Non-woody plants include, for instance, cotton, flax, esparto grass, milkweed, straw, jute hemp, and bagasse.

The term "superabsorbent material" refers to a water-swellable, water-insoluble organic or inorganic material capable, under the most favorable conditions, of absorbing at least about 20 times its weight, preferably at least about 30 times its weight in an aqueous solution containing 0.9% by weight sodium chloride.

The term "personal care absorbent product" includes without limitation diapers, training pants, swim wear, absorbent underpants, baby wipes, adult incontinence products, and feminine hygiene products.

The term "medical absorbent product" includes without limitation absorbent garments, underpads, bandages, absorbent drapes, and medical wipes.

DETAILED DESCRIPTION OF THE PRESENTLY PREFERRED EMBODIMENTS

Referring to FIG. 1 of the drawings, an absorbent garment 2 of the invention has a pant-like configuration useful for diapers, child training pants, child swim wear, adult incontinence articles, and the like. The garment 2 includes a waste containment section ("chassis") 4 having front portion 5 and rear portion 7 joined by central ("crotch") portion 15, and two side portions 6 and 8, each of which is connected at its edges to the front and rear portions. The side panel 6 includes stretchable panels 18 and 20 joined to each other along seam 30, and joined to the waste containment section along seams 29 and 31. Each of the seams 29,30 and 31 is longitudinally oriented, and extends from the top of the waist opening 10 to the leg opening 12. The side panel 8 includes stretchable panels 24 and 26 joined to each other along seam 33, and joined to the waste containment section along seams 32 and 34. Each of the seams 32, 33 and 34 is longitudinally oriented, and extends from the top of the waist opening to the leg opening 14.

Chassis 4 includes multiple layers (described below) including, for instance, a liquid-permeable top layer, an absorbent core layer, and a breathable liquid-impermeable outer cover layer 16 which faces away from the wearer. An inner nonwoven filament web, positioned between the absorbent core and outer cover 16, is described below. The waste containment section 4 also includes elasticized waist portions 22 on the front and back of the garment. The leg opening portions 12 and 14 also include elastic portions 46 which extend substantially around the portion of the leg openings defined by the waste containment section 4.

Figure 2:
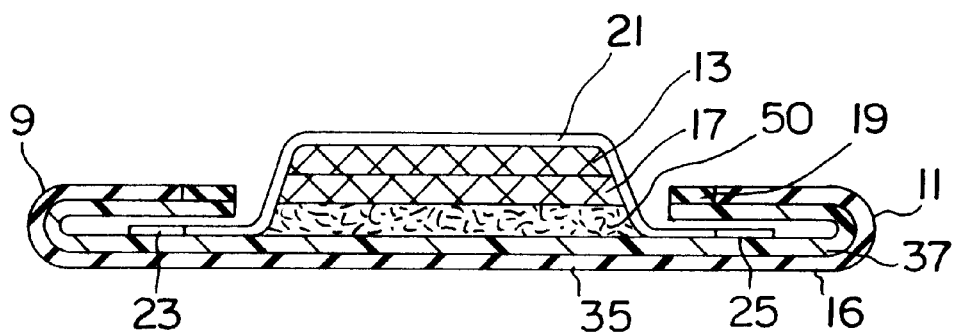
FIG. 2 is an expanded sectional view of the absorbent article of the invention, taken along the line 2—2 in FIG. 1.

FIG. 2 shows an expanded cutout view of the individual layers of the absorbent article, taken along the line 2—2 in FIG. 1. Referring to FIG. 2, the absorbent garment 2 includes several layers in the central region 15. The layers include a liquid-permeable top layer 21, a liquid-permeable surge layer 13 adjacent and below the top layer 21, an absorbent layer 17 adjacent and below the surge layer 13, an inner nonwoven filament web 50 adjacent and below the absorbent layer 17, and a breathable, substantially liquid impermeable outer cover 16 adjacent and below the inner nonwoven filament web 50.

In the embodiment shown, the top layer 21 and outer cover material 16 are wider than surge layer 13, absorbent core 17, and inner web 50. The top layer 21 substantially surrounds the surge layer 13, absorbent core 17, and inner nonwoven filament web 50, and is affixed at end regions 23 and 25 to the outer cover material 16 using an adhesive, ultrasonic or thermal bonding technique. The outer cover material 16 is folded over at both lateral ends 9 and 11, so that it overlaps and envelops the edges 23 and 25 of the top layer 21. Within the overlap, the layers can be bonded together using thermal, ultrasonic, or adhesive bonding. The elastic regions 46 can be formed with elastic bands 19 affixed to, and/or within, the outer cover material 16 using an adhesive, ultrasonic, or thermal bonding technique.

The longitudinal seams 29–34 may be formed by conventional methods including, without limitation, ultrasonic welding, thermal bonding, adhesive bonding, stitch bonding and the like. Ultrasonic welding is a presently preferred technique. The various bonding techniques are conventional, and are neither critical nor limiting as to the present invention.

The stretchable side panels 6 and 8 can be constructed of conventional woven or nonwoven materials, formed from a wide variety of elastic and stretchable polymers. The terms "elastic" and "stretchable" include any material which can be stretched, and which tends to return to its original shape when relaxed. Suitable polymers include without limitation block copolymers of polystyrene, polyisoprene and polybutadiene; copolymers of ethylene, natural rubbers and urethanes; and combinations of the foregoing. Particularly suitable are styrene-butadiene block copolymers sold by Shell Chemical Co. under the trade name KRATON®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Also suitable are coextruded composites of the foregoing, and elastomeric staple integrated composites where staple fibers of polypropylene, polyester, cotton and other materials are integrated into an elastomeric meltblown web. Certain elastomeric single-site or metallocene-catalyzed olefin polymers and copolymers are also suitable for the side panels. The stretchable side panels are preferably rectangular in shape, and preferably extend from the top of the waist opening 10 to the leg openings 12 and 14. The side panels may also be laminates of multiple layers, and are preferably breathable to water vapor but impervious to liquids.

Both the surge layer 13 and body side liner 21 are constructed from highly liquid pervious materials. These layers function to transfer liquid from the wearer to the absorbent layer 17. Suitable materials include porous woven materials, porous nonwoven materials, and apertured films. Examples include, without limitation, any flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof. Either layer may also be an apertured plastic film. The various layers of garment 2 have dimensions which vary depending on the size and shape of the wearer.

Absorbent layer 17 can be made of wood pulp fluff or a mixture of wood pulp fluff and a superabsorbent material, or a wood pulp fluff integrated with a thermoplastic absorbent material treated with a surfactant. Thermal binders, such as Pulpex® can be used in blends or layering with the fluff and superabsorbent. Layer 17 can also be a batt of meltblown synthetic fibers, a bonded carded web of synthetic or natural fibers or blends thereof, a composite of meltblown fibers and the like. The synthetic fibers can be, but are not limited to, polypropylene, polyethylene, polyester and copolymers of these or other polyolefins.

The term "superabsorbent" or "superabsorbent material" refers to a water-swellable, water-insoluble organic or inorganic material capable, under the most favorable conditions, of absorbing at least about 20 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrilegrafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

The outer cover material 16 is breathable to water vapor. Generally the outer cover 16 will have a WVTR of at least about 300 grams/m$^2$-24 hours using the test procedure described below, preferably at least about 1500 grams/m$^2$-24 hours, more preferably at least about 3000 grams/m$^2$-24 hours. Outer cover 16 shown in FIG. 2 includes two layers 35 and 37, joined by thermal or ultrasonic bonding, or an adhesive. Layer 35 is a nonwoven filament web. Layer 37 is a breathable film. Outer cover 16 is positioned with nonwoven web 35 facing outward, and with breathable film 37 facing inward toward the dampness-inhibiting inner nonwoven web 50.

The nonwoven filament web 35 may be a spunbond web, a meltblown web, a bonded carded web, an air laid web, or any other filament-type nonwoven web which does not appreciably absorb aqueous fluid. Preferably, the nonwoven web 35 is made from one or more thermoplastic polymers. Suitable polymers include, without limitation, polyethylene, polypropylene, copolymers of mainly ethylene and $C_3$–$C_{12}$ alpha-olefins (commonly known as linear low density polyethylene), copolymers of mainly propylene with ethylene and/or $C_4$–$C_{12}$ alpha-olefins, and flexible polyolefins including propylene-based polymers having both atactic and isotactic propylene groups in the main polypropylene chain, polyamides, and polyesters. Other suitable polymers include without limitation elastomers, for example polyurethanes, copolyether esters, polyamide polyether block copolymers, ethylene vinyl acetate copolymers, block copolymers having the general formula A-B-A' or A-B such as copoly (styrene/ethylene-butylene), styrene-poly (ethylene-propylene)-styrene, styrene-poly (ethylene-butylene)-styrene, polystyrene/poly(ethylene-butylene)/polystyrene, poly (styrene/ethylene-butylene/styrene), and the like. Metallocene-catalyzed polyolefins are also useful, including those described in U.S. Pat. Nos. 5,571,619; 5,322,728; and 5,272,236, the disclosures of which are incorporated herein by reference.

Polymers made using metallocene catalysts have a very narrow molecular weight range. Polydispersity numbers (Mw/Mn) of below 4 and even below 2 are possible for metallocene-produced polymers. These polymers also have a controlled short chain branching distribution compared to otherwise similar Ziegler-Natta produced type polymers. It is also possible using a metallocene catalyst system to control the isotacticity of the polymer quite closely.

The nonwoven web 35 is preferably made of polyethylene, polypropylene, or a semi-crystalline propylene-ethylene copolymer. The web 35 is laminated to breathable film 37 using patterned thermal calender bonding, ultrasonic bonding, adhesive bonding, or the like. Preferably, the bonded regions will cover less than about 25%, more preferably less than about 20% of the interface between web 35 and film 37, so that the bonding does not impede breathability of the laminate 16.

Figure 3:
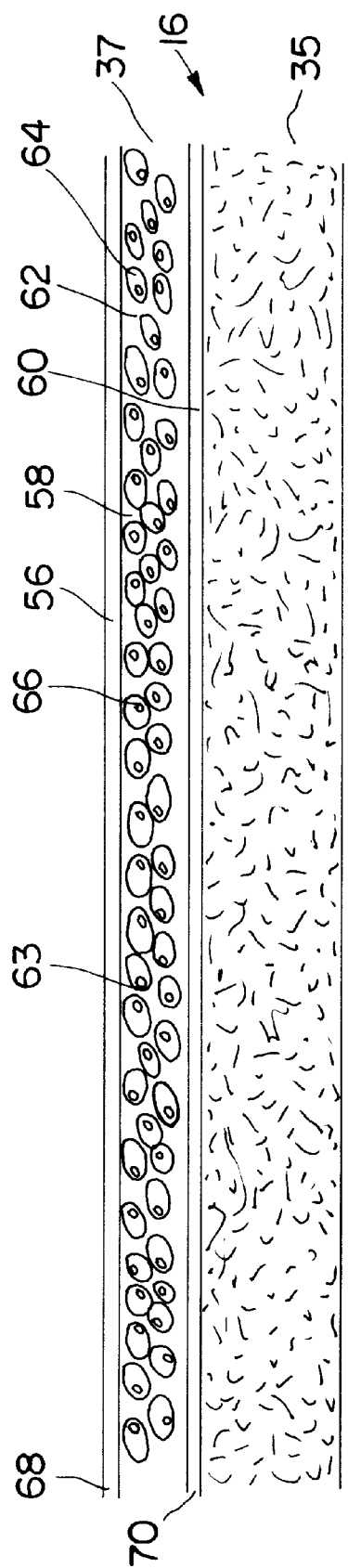
FIG. 3 is an expanded sectional view of one embodiment of the breathable outer cover material.

The breathable film 37 is illustrated in more detail in FIG. 3, which is an expanded sectional view of outer cover 16. In one embodiment, breathable film 37 includes at least one microporous layer 58. The microporous layer 58 can be formed using a variety of known technologies. Preferably, layer 58 includes a polymer matrix 62, a plurality of voids 64 within the matrix surrounded by relatively thin microporous membranes 63 defining tortuous paths, and one or more filler particles 66 in each void 64. The layer 58 is microporous and breathable, wherein the microporous membranes 63 between the voids readily permit molecular diffusion of water vapor from a first surface 68 to a second surface 70 of the film layer 58.

The polymer matrix 62 can be formed from any suitable film-forming thermoplastic polymer. Examples of suitable polymers include without limitation the thermoplastic polymers listed above, which can be used for the nonwoven web 35. Polyolefins are preferred, and liner low density polyethylenes formed using a Ziegler-Natta or metallocene catalyst are most preferred.

The filler particles 66 can include any suitable inorganic or organic filler. The filler particles 66 are preferably small, in order to maximize vapor transmission through the voids. Generally, the filler particles should have a mean particle diameter of about 0.1–7.0 microns, preferably about 0.5–7.0 microns, most preferably about 0.8–2.0 microns. Suitable fillers include without limitation calcium carbonate, non-swellable clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin, mica, carbon, calcium oxide, magnesium oxide, aluminum hydroxide and polymer particles. Calcium carbonate is a presently preferred filler.

The filler particles 66 may be coated with a minor quantity (e.g. up to 2% by weight) of a fatty acid or other material to ease their dispersion in the polymer matrix. Suitable fatty acids include without limitation stearic acid, or a larger chain fatty acid such as behenic acid. The amount of filler particles 66 in the layer 52 should range from about 30–80% by weight of the layer 58, preferably about 40–70% by weight, most preferably about 50–65% by weight. Similarly, the polymer matrix 62 should constitute about 20–70% by weight of the layer 58, preferably about 30–60% by weight, more preferably about 35–50% by weight.

The polymer composition, filler content, filler particle size and degree of stretching are factors which help determine the breathability of the microporous film layer 58. Generally, the microporous film layer 58 will be less than about 50 microns thick, preferably less than about 30 microns thick, most preferably less than about 20 microns thick. The breathable film 37 may be uniaxially stretched to about 1.1–7.0 times its original length, preferably to about 1.5–6.0 times its original length, most preferably to about 2.5–5.0 times its original length. The film may alternatively be biaxially stretched using conventional techniques familiar to persons skilled in the art.

In the embodiment of FIG. 3, the microporous breathable film layer 58 is adjacent one or two relatively thin outer skin layers 56 and 60, in a two or three-layer film 37. The inclusion of one or two skin layers improves film processability and can also contribute heat seal properties to the breathable film 37. The breathable film 37 can be prepared by cast or blown film coextrusion of the layers, by extrusion coating, or by any conventional layering process. The polymers in the outer layers 56 and 60 can be the same or different than the polymers in the microporous layer 58. Preferably, the polymers in the outer layer or layers have a lower softening point than in the microporous layer 58, and contribute to the heat sealability of the film 37.

Also, the thickness and composition of the outer layers 56 and 60 should be selected so as not to substantially impair the moisture transmission through the breathable film 37. This way, the microporous layer 58 may determine the breathability of the entire film. To this end, the skin layers 56 and 60 each are generally less than about 10 microns thick, preferably less than about 5 microns thick, most preferably less than about 2.5 microns thick. Preferred skin layer polymers include ethylene vinyl acetates, propylene vinyl acetates, ethylene methyl acrylates, other vapor-permeable polymers, and blends of these with other polyolefins.

In accordance with the invention, a dampness-inhibiting nonwoven filament web 50 is disposed between the absorbent core 17 and the outer cover 16. The nonwoven web 50 has a mean fiber denier which is higher than the mean fiber denier of nonwoven web 35 of outer cover 16. Preferably, nonwoven web 50 has a mean fiber diameter at least about 10% higher, and more preferably at least about 20% higher, than the mean fiber denier of nonwoven web 35. Most preferably, nonwoven web 50 has a mean fiber denier at least about 30% higher than the mean fiber denier of nonwoven web 35.

Nonwoven web 50 should have a mean fiber denier of at least 2.0, preferably 2.2–10, more preferably 2.5–6.0. Nonwoven web 35 should have a mean fiber denier less than 2.0, preferably 0.1–1.8, more preferably 0.5–1.5.

The nonwoven web 50 may be a spunbond web, a meltblown web, a bonded carded web, an air laid web, a cellulose web, or any other microfibrous nonwoven web. Preferably, the nonwoven web 50 is made of thermoplastic polymer fibers. The polymers used to make the nonwoven web include the polymers listed above for the breathable microporous film 37, and the nonwoven web 35. The nonwoven web 50 is preferably constructed of a polyolefin, more preferably a polyethylene or polypropylene homopolymer or copolymer. The nonwoven web 50 should have a basis weight of about 0.1–4.0 ounces per square yard (osy), preferably about 0.3–2.0 osy, more preferably about 0.4–1.0 osy. The nonwoven web 50 may also be a laminate of more than one nonwoven web layer. For example, web 50 may be a spunbond-meltblown-spunbond structure as disclosed in U.S. Pat. No. 4,041,203, issued to Brock et al. If the nonwoven web 50 includes more than one layer, then the basis weight and mean fiber denier are calculated based on the combined layers, to give values which represent the web 50 in its entirety.

Preferably, nonwoven webs 35 and 50 are hydrophobic. Hydrophobic materials have a greater tendency to transmit moisture vapor instead of assimilating or retaining it. Hydrophilic materials, by contrast, have a higher tendency to assimilate or retain moisture vapor. As used herein, the term "hydrophobic" describes a material which has a contact angle of water-in-air of greater than 90 degrees. The term "hydrophilic" refers to a material which has a water-in-air contact angle of less than 90 degrees. The water-in-air contact angle is suitably determined as set forth in the book "Absorbency" edited by P. K. Chatterjee (Elsevier, N.Y., 1985).

During normal use of an absorbent article, such as a diaper or training pant, the breathability of outer cover 16 is influenced primarily by breathable film 37, and secondarily by nonwoven web 35. If the dampness-inhibiting layer 50 were constructed from filaments having lower mean denier than the filaments of nonwoven web 35, then the layer 50 would begin to inhibit breathability of outer cover 16. This is because webs of lower fiber denier tend to be more compact than webs of higher fiber denier. A dampness-inhibiting layer 50 which reduces outer cover breathability is counterproductive, because the humidity inside the garment will increase, causing increased skin hydration and decreased comfort.

On the other hand, by providing a nonwoven web 50 with a higher fiber denier, more open structure, the breathability of outer cover 16 will be substantially unaffected most of the time. The nonwoven web 50 of higher fiber denier also has higher bulk, thus trapping a larger amount of insulating air. This insulating factor lowers the thermal conductivity of the outer cover system (i.e., the outer cover plus the dampness-inhibiting nonwoven layer), thus eliminating the "clammy" feeling.

The elastic bands 19 may be in the form of single or multiple bands per leg. A wide variety of elastic materials may be employed. Examples include a film or meltblown web formed using block or graft copolymers of butadiene, isoprene, styrene, ethylene-methyl acrylate, ethylene-vinyl acetate, ethylene-ethyl acrylate or blends thereof. One preferred elastomer is a block copolymer of styrene-ethylbutadiene-styrene. Specific materials of which elastic bands 19 can be made are the Kraton G series from Shell Chemical Company, such as Kraton G-1650, Kraton G-1652, Kraton GX-1657 and preferably Kraton G-2740X. Also, the Kraton D series can be used, as well as polyester elastomeric materials, polyurethane elastomeric materials and polyamide elastomeric materials. Elastomeric single-site or metallocene-catalyzed olefin polymers and copolymers can also be employed. Also, elastic bands 19 can be made of an activatable material applied in an unstretched condition, and activated by heat, light or moisture or radiation to cause shrinkage and elasticity. Activatable elastic materials can be obtained from the 3M Company.

Test Procedure For Water Vapor Transmission Rate (WVTR)

The following procedure is described for testing of the water vapor transmission rate (WVTR) for breathable films and laminates. The WVTR is measured in a manner similar to ASTM Standard Test Method for Water Vapor Transmission of Materials, Designation E-96-80 as follows. For the purposes of the present invention, 3 inch diameter (76 mm) circular samples are cut from the test material and from a control material, CELGUARD®2500 (Hoechst Celanese Corporation). CELGUARD®2500 is a 0.0025 cm thick film composed of microporous polypropylene. Two or three samples are prepared for each material.

The cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred millimeters of distilled water is poured into each Vapometer cup, and each of the individual samples of the test materials and control material are placed across the top area of an individual cup. Screw-on flanges are tightened to form a seal along the edges of the cups leaving the associated test material or control material exposed to the ambient atmosphere over a 62 millimeter diameter circular area (an open, exposed area of about 30 $cm^2$). The cups are then weighed, placed on a tray, and set in a forced air oven set at 100° F. (38° C.).

The oven is a constant temperature oven with external air through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary test WVTR value is calculated as follows:

$$\text{Test WVTR} = [(\text{grams weight loss over 24 hours}) \times 7571] \div 24$$

The relative humidity within the oven is not specifically controlled. Under predetermined set conditions of 100° F. and ambient relative humidity, the WVTR for CEL-GUARD®2500 has been determined to be 5000 $g/m^2/24$ hours. Accordingly, CELGUARD®2500 is run as a control sample with each test and the resulting values are corrected in accord with the variation of the control relative to its known WVTR.

While the embodiments of the invention described herein are presently considered preferred, various modifications and improvements can be made without departing from the spirit and scope of the invention. The scope of the invention is indicated by the appended claims, and all changes that fall within the meaning and range of equivalents are intended to be embraced therein.

We claim:

1. An absorbent article, comprising:
   a liquid-permeable top layer;
   an absorbent core layer;
   a hydrophobic inner nonwoven filament web; and
   a breathable outer cover having a WVTR of at least about 300 grams/$m^2$-24 hours;

the breathable outer cover including at least a breathable film and an outer nonwoven filament web having a mean fiber denier;

wherein the inner nonwoven filament web has a mean fiber denier higher than the mean fiber denier of the outer nonwoven filament web.

2. The absorbent article of claim 1, wherein the inner nonwoven filament web has a mean fiber denier of at least 2.0.

3. The absorbent article of claim 1, wherein the inner nonwoven filament web has a mean fiber denier of about 2.2–10.

4. The absorbent article of claim 1, wherein the inner nonwoven filament web has a mean fiber denier of about 2.5–6.0.

5. The absorbent article of claim 1, wherein the outer nonwoven filament web has a mean fiber denier less than 2.0.

6. The absorbent article of claim 1, wherein the outer nonwoven filament web has a mean fiber denier of about 0.1–1.8.

7. The absorbent article of claim 1, wherein the outer nonwoven filament web has a mean fiber denier of 0.5–1.5.

8. The absorbent article of claim 1, wherein the inner nonwoven filament web has a mean fiber denier at least about 10% higher than the mean fiber denier of the outer nonwoven filament web.

9. The absorbent article of claim 1, wherein the inner nonwoven filament web has a mean fiber denier at least about 20% higher than the mean fiber denier of the outer nonwoven filament web.

10. The absorbent article of claim 1, wherein the inner nonwoven filament web has a mean fiber denier at least about 30% higher than the mean fiber denier of the outer nonwoven filament web.

11. The absorbent article of claim 1, wherein the breathable outer cover has a WVTR of at least about 1500 grams/m$^2$-24 hours.

12. The absorbent article of claim 1, wherein the breathable outer cover has a WVTR of at least about 3000 grams/m$^2$-24 hours.

13. The absorbent article of claim 1, wherein the outer cover is positioned with the breathable film facing the inner nonwoven filament web.

14. The absorbent article of claim 1, wherein the inner nonwoven filament web comprises a polymer selected from the group consisting of polyethylene, polypropylene, copolymers of mainly ethylene and $C_3$–$C_{12}$ alpha-olefins (commonly known as linear low density polyethylene), copolymers of mainly propylene with ethylene and/or $C_4$–$C_{12}$ alpha-olefins, flexible polyolefins including propylene-based polymers having both atactic and isotactic propylene groups in the main polypropylene chain, polyamides, polyesters, and combinations thereof.

15. The absorbent article of claim 1, wherein the inner nonwoven filament web comprises a polymer selected from the group consisting of polyurethanes, copolyether esters, polyamide polyether block copolymers, ethylene vinyl acetate copolymers, block copolymers having the general formula A-B-A' or A-B such as copoly (styrene/ethylene-butylene), styrene-poly (ethylene-propylene)-styrene, styrene-poly (ethylene-butylene)-styrene, polystyrene/poly (ethylene-butylene)/polystyrene, poly (styrene/ethylene-butylene/styrene), and combinations thereof.

16. The absorbent article of claim 1, wherein the inner nonwoven filament web comprises a polyolefin.

17. The absorbent article of claim 1, wherein the inner nonwoven filament web comprises a metallocene-catalyzed polyolefin.

18. An absorbent article, comprising:
a liquid-permeable top layer;
an absorbent core layer;
a hydrophobic inner nonwoven filament web having a first mean fiber denier, and
a breathable outer cover having a WVTR of at least about 300 grams/m$^2$-24 hours;
the breathable outer cover including a breathable film facing the inner nonwoven filament web and an outer nonwoven filament web having a second mean fiber denier, facing away from the inner nonwoven filament web;
wherein the first mean fiber denier is at least about 10% higher than the second mean fiber denier.

19. The absorbent article of claim 18, wherein the inner nonwoven filament web has a basis weight of about 0.1–4.0 osy.

20. The absorbent article of claim 18, wherein the inner nonwoven filament web has a basis weight of about 0.3–2.0 osy.

21. The absorbent article of claim 18, wherein the inner nonwoven filament web has a basis weight of about 0.4–1.0 osy.

22. The absorbent article of claim 18, wherein the inner nonwoven filament web comprises a spunbond web.

23. The absorbent article of claim 18, wherein the inner nonwoven filament web comprises a meltblown web.

24. The absorbent article of claim 18, wherein the inner nonwoven filament web comprises a bonded carded web.

25. The absorbent article of claim 18, wherein the inner nonwoven filament web comprises an air laid web.

26. The absorbent article of claim 18, wherein the inner nonwoven filament web comprises a plurality of nonwoven layers.

27. An absorbent article, comprising:
a liquid-permeable top layer;
an absorbent core layer;
a hydrophobic inner nonwoven filament web having a basis weight of about 0.1–4.0 osy and a first mean fiber denier; and
a breathable outer cover including a breathable microporous film facing the inner nonwoven filament web, and an outer nonwoven filament web facing away from the inner nonwoven filament web and having a second mean fiber denier;
wherein the first mean fiber denier is higher than the second mean fiber denier.

28. The absorbent article of claim 27, comprising a diaper.

29. The absorbent article of claim 27, comprising a training pant.

30. The absorbent article of claim 27, comprising an adult incontinence garment.

31. The absorbent article of claim 27, comprising swim wear.

32. The absorbent article of claim 27, comprising a medical absorbent product.

* * * * *